United States Patent
Leonard et al.

(10) Patent No.: US 9,566,206 B2
(45) Date of Patent: Feb. 14, 2017

(54) GRADUATED COMPRESSION GARMENTS

(75) Inventors: Michael Wayne Leonard, Senoia, GA (US); David McKinley York, Senoia, GA (US)

(73) Assignees: SIGVARIS INC., Peachtree City, GA (US); SIGVARIS AG, St. Gallen (CH)

( * ) Notice: Subject to any disclaimer, the term of this patent is extended or adjusted under 35 U.S.C. 154(b) by 431 days.

(21) Appl. No.: 14/006,707

(22) PCT Filed: Mar. 23, 2012

(86) PCT No.: PCT/EP2012/055217
§ 371 (c)(1),
(2), (4) Date: Sep. 23, 2013

(87) PCT Pub. No.: WO2012/127033
PCT Pub. Date: Sep. 27, 2012

(65) Prior Publication Data
US 2014/0012166 A1 Jan. 9, 2014

Related U.S. Application Data

(60) Provisional application No. 61/466,485, filed on Mar. 23, 2011.

(30) Foreign Application Priority Data

Jun. 29, 2011 (EP) .................................. 11171910

(51) Int. Cl.
*A61H 1/00* (2006.01)
*A61F 13/08* (2006.01)

(52) U.S. Cl.
CPC ............... *A61H 1/008* (2013.01); *A61F 13/08* (2013.01)

(58) Field of Classification Search
CPC combination set(s) only.
See application file for complete search history.

(56) References Cited

U.S. PATENT DOCUMENTS 2,613,520 A * 10/1952 Schaefer ................ A41B 11/00
2/239
5,622,666 A 4/1997 Struszczyk et al.
5,807,295 A 9/1998 Hutcheon et al.
(Continued)

FOREIGN PATENT DOCUMENTS

AT 2008388 3/2008
AT 507387 4/2010
(Continued)

OTHER PUBLICATIONS

Definition of "Nonwoven fabric", Retrieved from the internet: https://en.wikipedia.org/wiki/Nonwoven_fabric on May 24, 2016, 4 pages, entry last modified May 11, 2016.
(Continued)

*Primary Examiner* — Ophelia A Hawthorne
(74) *Attorney, Agent, or Firm* — Kilpatrick Townsend & Stockton LLP

(57) ABSTRACT

The present invention is directed to graduated compression garments for legs having flat toe seams, wherein the pressure value at the ankle zone (1) is of about 10-27 mmHg and at the calf zone (2) about 6-16 mmHg, wherein at least an achilles section, heel section, toe section and/or a foot sole section is cushioned on the internal side of the garment.

17 Claims, 7 Drawing Sheets

(56) References Cited

U.S. PATENT DOCUMENTS

Figure 1:
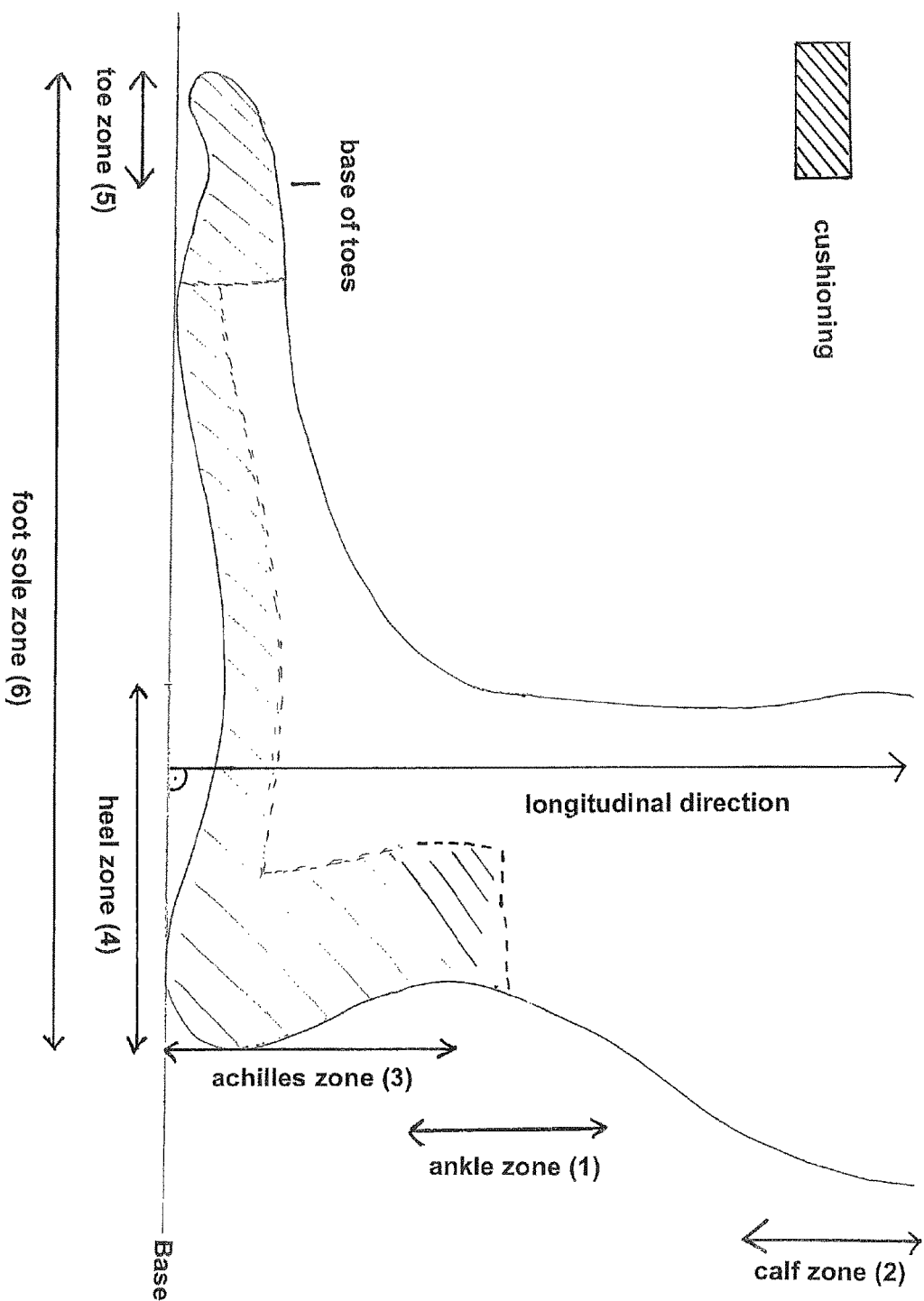

| | | | |
|---|---|---|---|
| 6,267,744 B1 | 7/2001 | Roberts et al. | |
| 6,557,274 B2 | 5/2003 | Litchfield et al. | |
| 7,400,938 B2 | 7/2008 | Ganzoni et al. | |
| 7,441,419 B1 * | 10/2008 | Dollyhite | A61F 13/08 66/178 A |
| 7,886,776 B2 | 2/2011 | Jung et al. | |
| 2003/0134120 A1 | 7/2003 | Kim et al. | |
| 2006/0021389 A1 | 2/2006 | Menzies et al. | |
| 2007/0000027 A1 | 1/2007 | Ganzoni et al. | |
| 2007/0033711 A1 | 2/2007 | Achtelstetter et al. | |
| 2007/0042024 A1 | 2/2007 | Gladman et al. | |
| 2007/0283483 A1 * | 12/2007 | Jacober | A41B 11/00 2/239 |
| 2008/0097001 A1 | 4/2008 | Smart et al. | |
| 2008/0195016 A1 | 8/2008 | Bottini et al. | |
| 2008/0195019 A1 | 8/2008 | Ganzoni et al. | |
| 2009/0181599 A1 | 7/2009 | Farmer et al. | |
| 2010/0055157 A1 | 3/2010 | Gunn et al. | |
| 2010/0056973 A1 * | 3/2010 | Farrow | A61F 13/08 602/63 |
| 2010/0137776 A1 | 6/2010 | Virkus et al. | |
| 2011/0041232 A1 | 2/2011 | Covelli et al. | |
| 2011/0212150 A1 | 9/2011 | Redlinger et al. | |
| 2013/0108676 A1 | 5/2013 | Redlinger et al. | |
| 2013/0131563 A1 | 5/2013 | Ettner et al. | |
| 2014/0336020 A1 | 11/2014 | Von Hoffmann et al. | |

FOREIGN PATENT DOCUMENTS

| | | | |
|---|---|---|---|
| CN | 2684597 | | 3/2005 |
| CN | 101056551 | | 10/2007 |
| DE | 602004006851 | | 1/2008 |
| EP | 1759676 | | 3/2007 |
| EP | 1895036 | | 3/2008 |
| EP | 1700947 | | 8/2009 |
| EP | 2068801 | | 3/2011 |
| GB | 2218638 | | 11/1989 |
| KR | 2009039032 A | * | 4/2009 |
| WO | 9846818 | | 10/1998 |
| WO | 2004007818 | | 1/2004 |
| WO | 2006032096 | | 3/2006 |
| WO | 2006047153 | | 5/2006 |
| WO | 2007112067 | | 10/2007 |
| WO | 2008053159 | | 5/2008 |
| WO | 2009092121 | | 7/2009 |
| WO | 2009111808 | | 9/2009 |
| WO | 2010031091 | | 3/2010 |
| WO | 2010031862 | | 3/2010 |
| WO | 2011117111 | | 9/2011 |

OTHER PUBLICATIONS

Akbari et al., "Diabetes and peripheral vascular disease", Journal of vascular surgery 30.2 (1999): 373-384.

Apelqvist et al., "Prognostic value of systolic ankle and toe blood pressure levels in outcome of diabetic foot ulcer", Diabetes Care 12.6 (1989): 373-378.

Armstrong et al., "Choosing a practical screening instrument to identify patients at risk for diabetic foot ulceration", Archives of internal medicine vol. 158, No. 3, 1998, pp. 289-292.

Bartels, Handbook of medical textiles. Elsevier, Aug. 2011, pp. 167-168.

Belcaro et al., "Diabetic microangiopathy treated with elastic compression—a microcirculatory evaluation using laser-Doppler flowmetry, transcutaneous PO2/PCO2 and capillary permeability measurements", VASA. vol. 19, No. 3, 1990, pp. 247-251.

Brodovicz et al., "Reliability and feasibility of methods to quantitatively assess peripheral edema", Clinical medicine & research 7.1-2 (2009): 21-31.

Dinh et al., "Review: peripheral arterial disease and diabetes: a clinical update", The international journal of lower extremity wounds 8.2 (2009): 75-81.

Eneroth et al., "Amputation for occusive arterial disease", International orthopaedics 16.4 (1992): 383-387.

European Application No. EP11171910.1, Extended European Search Report dated Sep. 8, 2011.

International Application No. PCT/EP2012/055217, International Preliminary Report on Patentability dated Sep. 24, 2013.

International Application No. PCT/EP2012/055217, International Search Report dated Apr. 12, 2012.

Rabe et al., "Bonner Venenstudie der Deutschen Gesellschaft fur Phlebologie", Phlebologie 32.1 (2003): 1-14.

Rous et al., "Fluorescent Molecular Probes for the Characterisation of Fibre Structure and Distribution of Textile Resin Finishing on Lyocell", Lenzinger Berichte 83 (2004): 92-98.

Ting et al., "Clinical and hemodynamic outcomes in patients with chronic venous insufficiency after oral micronized flavonoid therapy", Vascular and Endovascular Surgery 35.6 (2001): 443-447.

Weder et al., "X-ray tomography measurements of the moisture distribution in multilayered clothing systems", Textile research journal 76.1 (2006): 18-26.

Wu et al., "Foot ulcers in the diabetic patient, prevention and treatment", Vascular health and risk management 3.1 (2007): 65.

Young et al., "The prediction of diabetic neuropathic foot ulceration using vibration perception thresholds: a prospective study", Diabetes care 17.6 (1994): 557-560.

U.S. Appl. No. 13/637,133, "Non-Final Office Action", Sep. 11, 2015.

U.S. Appl. No. 13/637,133, "Final Office Action", Mar. 24, 2016.

International Patent Application No. PCT/EP2011/054476, "International Report on Patentability", Jun. 22, 2012.

International Patent Application No. PCT/EP2011/054476, "International Search Report", Apr. 20, 2011.

International Patent Application No. PCT/EP2011/054476, "Written Opinion", Mar. 2, 2012.

* cited by examiner

GRADUATED COMPRESSION GARMENTS

RELATED APPLICATIONS

The present application is a national phase of PCT/EP2012/055217, filed Mar. 23, 2012, which claims the benefit of priority to U.S. Provisional Patent Application No. 61/466,485, filed Mar. 23, 2011, and European Patent Application No. 11171910.0, filed Jun. 29, 2011, all of which are incorporated herein by reference in their entirety.

The invention relates to a graduated compression garment for legs, which is at least partially cushioned on the internal side of the garment.

Compression garments are garments which are mainly made from elastic knitted fabric. Their aim is to provide a pressure or compressive force, respectively, to a human body part, especially to a limb such as an arm or leg, for e.g. the treatment of venous diseases and lymphatic disorders. Compression garments for legs are usually elastic garments that can, for example, be used to compress a leg below the knee, above the knee or an entire leg. The garments can be designed as stockings, socks, pants, etc.

The veins are blood vessels carrying the blood towards the heart. Malfunctioning veins have a reduced transport capacity, resulting in a blood congestion. If larger veins, such as leg veins, are congested with blood, liquid from the vessels is pressed into the surrounding tissues, thereby forming edema. Chronic edema may induce severe skin lesions and venous ulcers.

Compression stocking therapy is the standard treatment for edema, reducing swelling via a wrap system that can enhance fibrinolysis and venous outflow (Armstrong D. G. et al., Archives of Internal Medicine, 1998, 158, 289). Compression garments support the action of veins and facilitate the transport of blood, thereby treating or preventing patients from swollen legs or edema.

It is common for patients suffering from diabetes to present also lower extremity edema of the leg, ankle or/and foot (Brodovicz et al., Clin. Med. Res., 2009, 7 (1-2), 21).

Treating edema in patients suffering from diabetes is particularly important since edema may be one factor contributing to the development of diabetic feet.

Diabetic foot is an umbrella term for foot problems in patients suffering from diabetes mellitus. Due to arterial abnormalities and neuropathy as well as a tendency to reduced wound healing in patients suffering from diabetes, infection or gangrene of the foot is relative common.

Due to bad wound healing in patients suffering from diabetes, even small injuries like cuts or pressure marks, e.g. from inappropriate shoes, may develop into severe wounds that heal slowly, and—in the worst case—make it necessary to amputate the leg. In the presence of edema at the affected body parts wound healing is even more reduced. Foot problems are responsible for up to 15% of diabetes-related hospital admissions.

Patients suffering from diabetes may benefit from graduated compression, however, because of the common association of peripheral arterial disease (PAOD) in patients having diabetes (Akbari et al., J. Vasc. Surg. 1999, 30(2), 373; Banga, Diab. Rev. Int. 1994, 3, 6; Dinh et al., Int. J. Low. Extrem. Wounds, 2009, 8(2), 75) the clinicians are reluctant to apply compressive dressings in fear of exacerbating the symptoms of PAOD and the possible resulting gangrene (Eneroth, Int. Orthop., 1992, 16, 383).

In case of patients suffering from PAOD the blood supply from the heart via the arteries is already reduced and applying an external pressure would even deteriorate the blood supply, in particular to the lower extremities, such as legs.

According to the present invention, a compression garment offering improved wearing comfort and protection against skin lesions shall be provided which is also suitable for patients suffering from diabetes.

Thus, in a first aspect the present invention relates to a graduated compression garment for leg, having flat toe seams, wherein the pressure value at the ankle zone is of about 10-27 mmHg and at the calf zone of about 6-16 mmHg, wherein at least an achilles section, heel section, toe section and/or a foot sole section is cushioned on the internal side of the garment.

The compression garment may be preferably selected from compression stockings, compression socks, compression leggings, compression calf sleeves and compression tights.

The compression garments may be used for both medical and non-medical applications such as wellness or sport, e.g. to increase performance and recovery. The knitting construction may be of any known type, e.g. rib, floated stitch, terry loop, weft stitch, etc.

Compression garments and methods for their manufacture are e.g. disclosed in EP-A-1 895 036 (Ganzoni Management AG), U.S. Pat. No. 7,400,938 (Ganzoni Management AG), US 2007/0000027 (Ganzoni Management AG) and WO 2006/047153 (BSN-JOBST INC.), the content of which is herein incorporated by reference.

The garments are all characterised in that they contain elastic fibres, particularly more than 5%, more particularly more than 15% by weight based on the total weight. Preferably, the garments according to the invention comprise at least an elastic yarn, e.g. a synthetic yarn, such as Lycra®, Creora®, Roica® or Dorlastane®, or a natural elastic yarn, such as rubber, and at least a synthetic and/or natural fiber such as polyamide, polyester or cellulose-based fibre, cotton, or wool.

In a preferred embodiment, the compression garment according to the invention may comprise a yarn which is a blend of 85-90% hydrophobic fibres and 10-15% hydrophilic fibres, such as Dri-Release® yarn.

Dri-Release yarn is about 8 times more durable than cotton, dries about 4 times faster than cotton and offers superior moisture management performance.

In a further preferred embodiment the compression garment according to the invention further may comprise a chitosan-containing fibre such as a cellulose-based fibre, the surface of which is at least partially coated with chitosan.

Chitosan is obtained by deacetylation of chitin, which is a naturally occurring glycan produced in vertebrates, e.g. marine and terrestrial insects, arthropodia or crustaceans as well as funghi. Chitosan is a polycation which can be incorporated into fibres and textiles. The incorporation of chitosan into textile fibres has e.g. been described in WO 2004/007818 (Lenzing AG), WO 2009/092121 (Lenzing AG) and AT 008388 U2 (Lenzing AG). The content of these documents is herein incorporated by reference.

In a particular embodiment of the present invention, the chitosan-containing fibre is a cellulose-based fibre, e.g. a viscose, modal, polynosic or lyocell fibre, which contains chitosan at least on a part of its surface or a yarn obtained from such a fibre. In a further particular embodiment the chitosan-containing fibre is a cellulose-based fibre, e.g. a viscose, modal, polynosic or lyocell fibre, which contains chitosan only on its surface or a yarn obtained from such a fibre. Such fibres may be prepared by techniques as disclosed in WO 2004/007818 or WO 2009/092121.

In a preferred embodiment the chitosan-containing fibre is a lyocell fibre coated with chitosan or a yarn obtained from such a fibre. Such a fibre is commercially available as Tencel C from Lenzing AG, for example Tencel C1 and Tencel C2. Generally, the chitosan content of the fibre may be in the range from 0.1-25%, preferably from 0.3-15% by weight based on the total weight of the fibre. In some embodiments, the chitosan content is from 0.3-0.6% by weight and in other embodiments, the chitosan content is from 0.7-1.5% by weight.

The Tencel C fibre (or another chitosan-containing fibre) may be spun to a yarn with a yarn count of Nm20 to Nm225 (dtex 500 to dtex 44), optionally together with other fibres as explained in detail below. The yarns may be ring yarns, compact yarns, OE-roto yarns etc.

Such yarns may comprise 100% Tencel C (or another chitosan-containing fibre) or a mixture (of the chitosan-containing fibre), wherein the amount of chitosan-containing component in the mixture or thread is at least 3%, 10%, 20%, 30%, 40%, 50% or higher based on the total weight of the mixture or thread.

In another preferred embodiment the yarn used for the compression garment according to the invention is a chitosan-containing fibre and/or a Dri-Release fibre.

The chitosan-coated fibre or a blend thereof with one or more other fibres may cover an elastic yarn, e.g. a synthetic yarn such as Lycra, Creora, Roica or Dorlastan, or a spandex yarn, or a natural elastic yarn such as rubber.

In one embodiment, the compression garment may comprise ply yarns from single ply yarns up to multiple ply yarns and covered ply yarns of 100% Tencel C (or another chitosan-containing fibre) or a mixture or a thread of the chitosan-containing fibre with at least one further fibre with at least one different component, e.g. a component selected from bamboo, wool, cotton, linen, silk, polyamide, polyester, polyacrylnitrile, polypropylene, viscose, modal and/or micromodal with elastane and/or elastodien, wherein the amount of chitosan-containing component in the mixture or thread is at least 3%, 10%, 20%, 30%, 40%, 50% or higher based on the total weight of the mixture or thread.

In a further embodiment, the compression garment may comprise single and/or double covered yarns for covering an elastic fibre such as elastane or elastodien. These yarns may comprise 100% Tencel C (or another chitosan-containing component) or a mixture or thread (of the chitosan-containing fibre with at least one further fibre), with at least one different component, e.g. a component selected from bamboo, wool, cotton, linen, silk, polyamide, polyester, polyacrylnitrile, polypropylene, viscose, modal, micromodal with elastane and/or elastodien, wherein the amount of chitosan-containing component in the mixture or thread is at least 3%, 10%, 20%, 30%, 40%, 50% or higher based on the total weight of the mixture or thread.

In still a further embodiment, the compression garment may comprise core-spun yarns as a wrap spinning for an elastic fibre such as elastane or elastodien. These yarns may comprise 100% Tencel C (or another chitosan-containing component) or a mixture or thread of the chitosan-containing component with at least one different component, e.g. selected from bamboo, wool, cotton, linen, silk, polyamide, polyester, polyacrylnitrile, polypropylene, viscose, modal, elastane and/or elastodien, wherein the amount of chitosan-containing component in the mixture or thread is at least 3%, 10%, 20%, 30%, 40%, 50% or higher based on the total weight of the mixture or thread.

In still a further embodiment, the compression garment may comprise core-yarns as false twist with 100% Tencel C (or another chitosan-containing compound) or a mixture of the chitosan-containing component with at least one different component, e.g. selected from bamboo, wool, cotton, linnen, silk, polyamide, polyester, polyacrylnitrile, polypropylene, viscose, modal, micromodal, elastane and/or elastodien, wherein the amount of chitosan-containing component in the mixture is at least 3%, 10%, 20%, 30%, 40%, 50% or higher based on the total weight of the mixture.

In still a further embodiment, the compression garment may comprise an elasto twist yarn as a wrap spinning for an elastic fibre such as elastane or elastodien. These yarns may comprise 100% Tencel C (or another chitosan component) or a mixture of the chitosan-containing component with at least one different component, e.g. selected from bamboo, wool, cotton, linen, silk, polyamide, polyester, polyacrylnitrile, polypropylene, viscose, modal, micro-modal with elastane and/or elastodien, wherein the amount of chitosan-containing component in the mixture is at least 3%, 10%, 20%, 30%, 40%, 50% or higher based on the total weight of the mixture.

The compression garments may comprise unblended chitosan-containing fibres or fibre mixtures of Tencel C (or another chitosan-containing component) in mixtures with other components, such as bamboo, wool, cotton, linnen, silk, polyamide, polyester, polyacrylnitrile, polypropylene, viscose, modal and/or micromodal, wherein the amount of chitosan-containing component in the mixture is at least 3%, 10%, 20%, 30%, 40%, 50% or higher based on the total weight of the mixture.

Suitable knitting techniques for the manufacture of the compression garments are flat knitting with one and more needle beds, and circular knitting, e.g. with one-cylinder or double cylinder machines.

In an especially preferred embodiment, Tencel C (or another chitosan-containing component) can be used on an inlaid yarn, which may be an elastic fibre such as lycra covered with the chitosan-containing component and optionally further fibres such as polyamide, e.g. PA 6.6. This inlaid yarn may be used together with a loop yarn, e.g. an elastic fibre such as lycra, which may be covered with a further fibre, e.g. a polyamide fibre such as PA 6.6. In some embodiments, the loop yarn may also contain a chitosan-containing fibre.

In the manufacture of the compression garment it is advantageous that the chitosan-containing fibre (or the chitosan-containing fibre mixture or thread) is in direct skin contact in order to provide high efficacy.

Compression garments comprising a chitosan-containing fibre or/and Dri-Release-like fibres have advantages with regard to antibacterial/bacterio-static activity, e.g. improvement of the microbial skin flora; wearing comfort, e.g. smoothness and softness, and compliance, e.g. anti-itching, skin abrasion and reduction of friction; skin moisture management, e.g. water retention, humidity absorption; skin thermoregulation and skin healing and protection.

According to the present invention, the compression garment exhibits a graduated compression, i.e. the pressure exerted to the lower limb varies depending on its respective position. Particularly, the pressure exerted to the skin decreases in longitudinal direction from the ankle towards the thigh. The gradient may change incrementally or continuously.

According to the invention, the pressure at the ankle zone (1) is of about 10-27 mmHg, preferably 10-25 mmHg, preferably 10-24 mmHg, more preferably 15-25 mmHg, preferably 15-24 mmHg, and most preferably 15-20 mmHg. The pressure at the calf zone is about 6-16 mmHg, preferably 9-14 mmHg, more preferably 9-13 mmHg.

In particular it was found that compression pressures of 10 mmHg, preferably 15 mmHg, more preferably 18 mmHg to 27 mmHg, preferably 25 mmHg, more preferably 24 mmHg and most preferably 20 mmHg at the ankle zone and pressures of 6 mmHg, preferably 9 mmHg to 16 mmHg, preferably 14 mmHg, most preferably 13 mmHg at the calf zone exert sufficient pressure to support the action of the legs' veins, thereby preventing or treating edema, whereas the blood supply via the arteries is not negatively influenced.

According to the present invention, the graduated compression garments have flat toe seams. The skilled worker will understand that flat toe seams refer to flat stitched seams at the toes. Flat seams or flat stitched seams refers to a specific sewing variant, wherein two pieces of fabric are joined edge to edge with no overlap and sewn with stitching that encloses the raw edges. Flat seams or flat stitched seams which can be used interchangebly, thus, are designed to avoid friction against the skin (and accordingly avoiding blistering) simultaneously improving the comfort of the wearer.

The compression garments according to the invention, thus, are particularly suitable for patients suffering from edema, even if the peripheral arterial function of the patient is reduced, such as in PAOD patients.

The indicated pressure values comply with normative requirements and specifications such as the German norm RAL-GZG 387/1 or the French norm NFG 30-102.

In some embodiments, the textile may fulfill requirements of national norms, e.g. norms in European countries, for medical compression garments, e.g. stockings. For example, the textile may be in accordance with RAL norm class 1, i.e. a pressure of 18-21 mmHg (24-28 hPa) or class 2, i.e. a pressure of 23-32 mmHg (31-43 hPa) at the ankle. Further, the textile may be in accordance with AFNOR class 1, i.e. a pressure of 10-15 mmHg (13-20 hPa), class 2, i.e. a pressure of 15-20 mmHg (20-27 hPa) or class 3, i.e. a pressure of 20-36 mmHg (27-48 hPa) at the ankle.

The pressure values for the textiles are determined by standard methods, e.g. involving the use of a HOSY meter or a dynamometer at the calf and ankle positions defined by the RAL or AFNOR norm.

High local pressure and friction are particularly critical for patients suffering from diabetes in view of development of diabetic feet. Moreover, diabetes mellitus often causes chronic polyneuropathy, i.e. a malfunction of the peripheral nerves throughout the body, e.g. legs and feet. Such a damage of the peripheral nerves is associated with a loss of sensation which may progress to such extent that a patient would not recognize pain or discomfort anymore. When wearing inappropriate footwear, the feet and legs may be seriously damaged resulting in ulcers, infections and amputations in some cases.

Accordingly, the compression garments according to the invention have a flat seam or are manufactured seamlessly. In case of a flat seam two pieces of fabric are joined edge to edge without an overlap and seamed at the raw edges. By processing the compression garments in this way any pressure or friction marks, which usually occur in conventional plain seamed articles, can be avoided.

In order to protect the feets or/and legs from further eventual excessive pressure or/and friction the compression garments of the present invention are internally cushioned, i.e. the cushioning is in direct contact with the skin, at the most exposed areas of the leg or/and foot.

The cushioned parts of the compression garment differ from the basic fabric of the compression garment by a higher shock absorption characteristic and avoid friction transfer to the skin. In a preferred embodiment, the cushioned areas comprise a terry loop padding, i.e. cushioned terry loops, The cushioning may have an increased contact area to the skin as compared to the basic fabric.

The configuration of the cushioning such that it is in direct contact with the skin results in more comfort for the wearer and prolongs its shock absorptive characteristics compared to an external cushioning. Moreover, in case of functional fibres, such as Dri-Release or/and chitosan containing fibres, an internal cushioning and thus a direct contact to the skin may be particularly advantageous.

The compression garment according to the invention therefore comprises at least an achilles section, heel section, toe section or/and a foot sole section on the internal side of the garment.

The cushioned achilles section according to the invention lies at least partially within the achilles zone (3). The achilles zone ranges from the base to the point where the achilles tendon has its smallest diameter. The achilles section is preferably at least 3, preferably at least 5, and most preferably at least 8 cm in width. Further, the achilles section is preferably at least 3 cm, preferably at least 6, and more preferably at least 10 cm in length. In a preferred embodiment, the achilles section covers the achilles tendon at least within the achilles zone. The cushioned achilles section preferably covers the whole achilles zone and optionally may extend beyond the upper end of the achilles zone by preferably 0.5 cm, more preferably 2 cm, even more preferably 3 cm or most preferably 4 cm. The achilles section may change over the heel section.

The cushioned achilles section is especially designed to absorb potential friction and pressure of the compression garment and of the shoes' stiffener or its edge.

The heel section lies at least partially within the heel zone (4). The heel zone ranges from the highest point of the longitudinal arch to the back end of the foot. The heel section preferably extends over at least 2 cm, preferably at least 5 cm, more preferably at least 8 cm in longitudinal direction perpendicular from the base. The heel section is preferably configured such that it covers the complete heel. If present, the heel section may preferably change over the achilles section or/and the foot sole section.

The cushioned heel section thus protects the foot from being injured by the shoes back-strap or friction.

The toe section lies at least partially within the toe zone (5). The toe zone ranges from the tiptoe to the base of toes. In a preferred embodiment the cushioned toe section covers the whole toe zone (5) and optionally extends beyond the base of toes. In a preferred embodiment the toe section extends at least 1 cm, 2 cm, 4 cm or preferably at least 6 cm beyond the base of toes. If present, the toe section may preferably change over the foot sole section.

The cushioned toe section protects the foot from being injured by stress and frictions or pressure sores in the toe cap area.

The foot sole section lies at least partially within the foot sole zone (6). The foot sole zone extends on the foot underside from the tiptoe to the back-end of the foot. Preferably the foot sole section covers the whole foot sole zone. The foot sole section may preferably extend beyond the sole to the sides of the foot. Preferably, the foot sole section extends over at least 1 cm, preferably at least 2 cm, more preferably at least 5 cm in longitudinal direction perpendicular from the base. The foot sole section may change over the toe section, the heel section or/and the achilles section, if present.

The cushioned foot sole section protects the foot from being injured by the insole or/and the lateral seams of the shoes.

The claimed pressure characteristics as well as the specific cushioning according to the invention complement each other perfectly in graduated compression garments according to the invention for use in treating and/or preventing edema, particularly lower extremity edema.

In spite of the presently existing prejudices regarding the treatment of diabetics with compression textiles, the compression garments according to the invention are configured such that they may particularly used for treating edema in patients suffering from diabetes, e.g. diabetes mellitus type I or/and type II, or for treating diabetic foot syndrome.

Moreover, it was found that the compression garments according to the invention further are suitable to counteract against skin dryness, particularly in case the compression garments contain functional fibres, such as Dri-Release- or/and chitosan-containing fibres.

This is particularly relevant for diabetics which often suffer from an impaired water balance, affecting also the skin moisture management. It is known that such affected skin is susceptible to various skin damages.

In one embodiment, patients suffering from a peripheral arterial occlusive disease and optionally polyneuropathy shall be excluded from the treatment with the compression garments according to the invention, although the graduated compression garments have no negative effect on peripheral arterial occlusive diseases (PAOD).

It was moreover found that the compression garments as described above have good biostatic and antimicrobial properties. Thus, the addition of antimicrobial agents is usually not necessary. Particularly, the compression garments according to the invention may be free of any silver containing agents, such as elemental silver or (in)organic silver salts.

FIGURE LEGEND

FIG. 1: Foot scheme indicating the achilles, heel, toe and foot sole zone.

Figure 2:
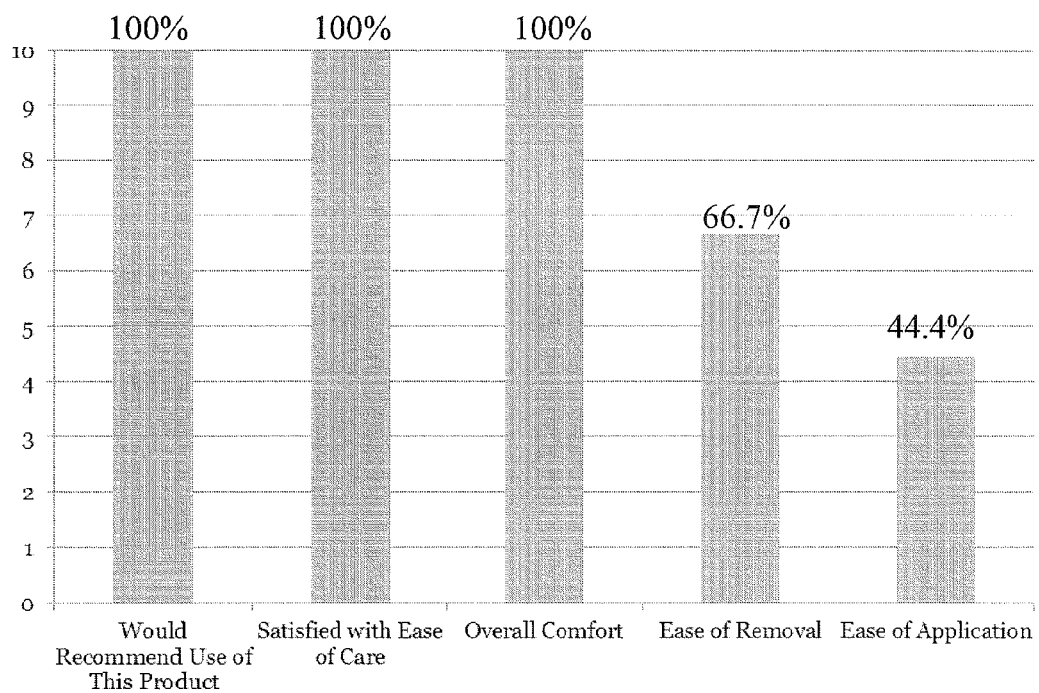

FIG. 2: Results of Patient Evaluation Form.

Figure 3:
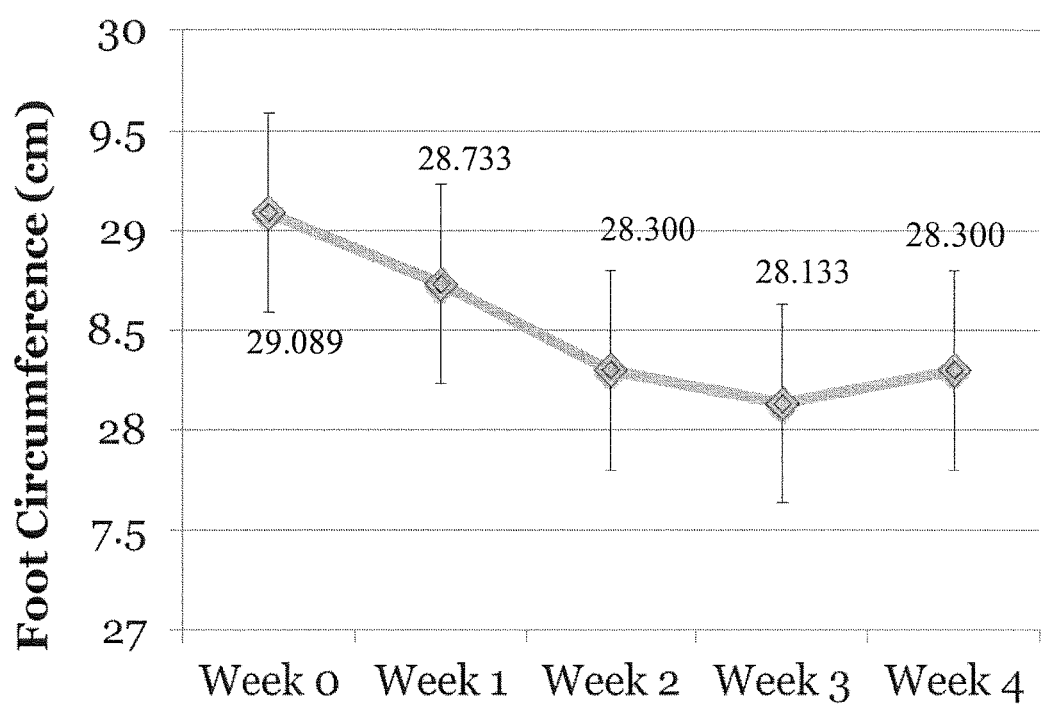

FIG. 3: Change in foot circumference.

Figure 4:
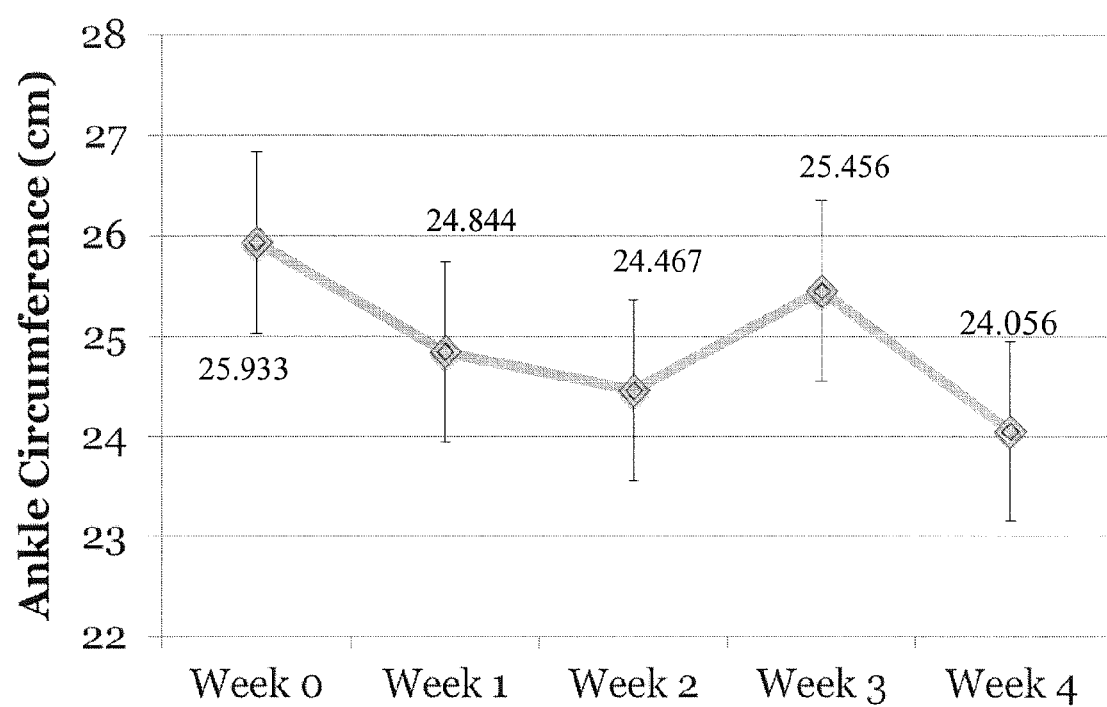

FIG. 4: Change in ankle circumference.

Figure 5:
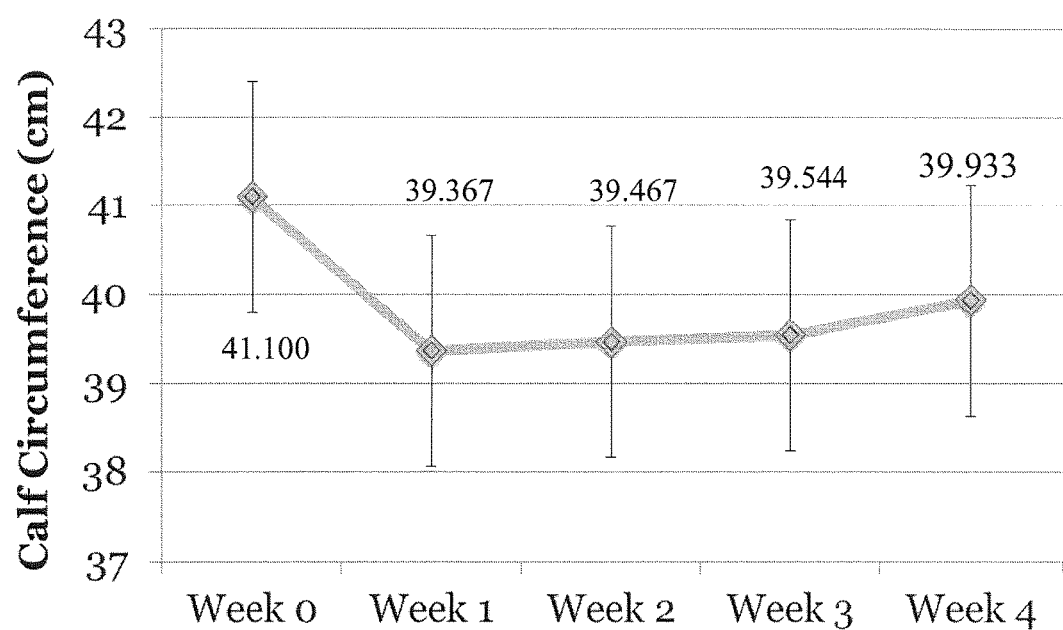

FIG. 5: Change in calf circumference.

Figure 6:
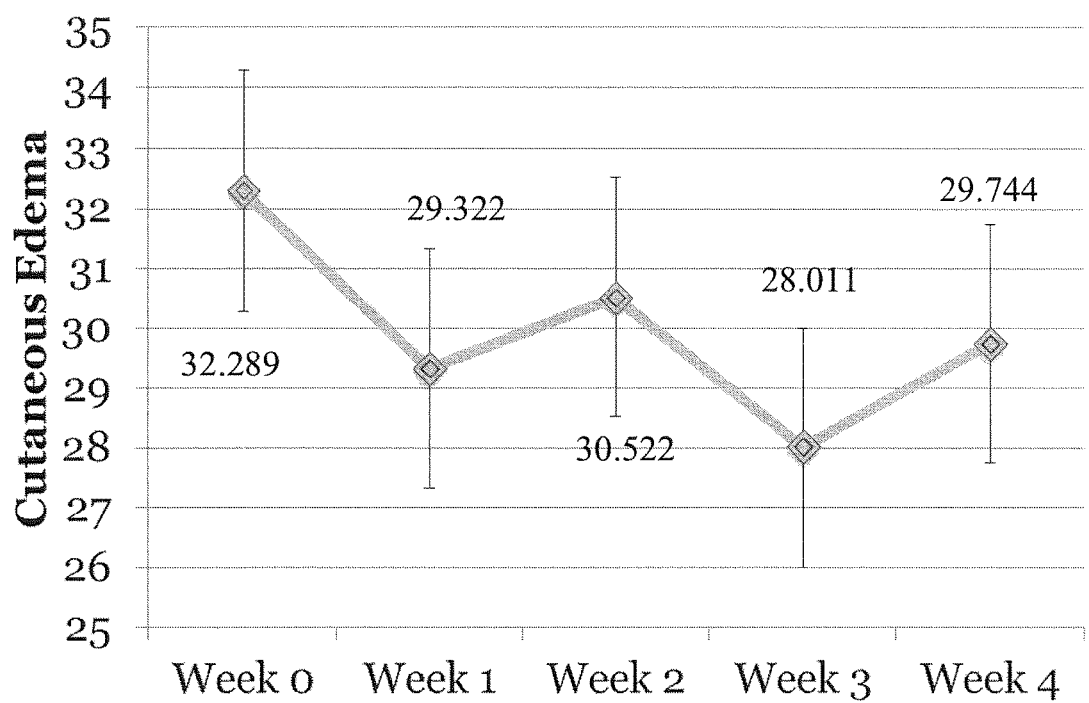

FIG. 6: Change in cutaneous edema (MoistureMeter values)

Figure 7:
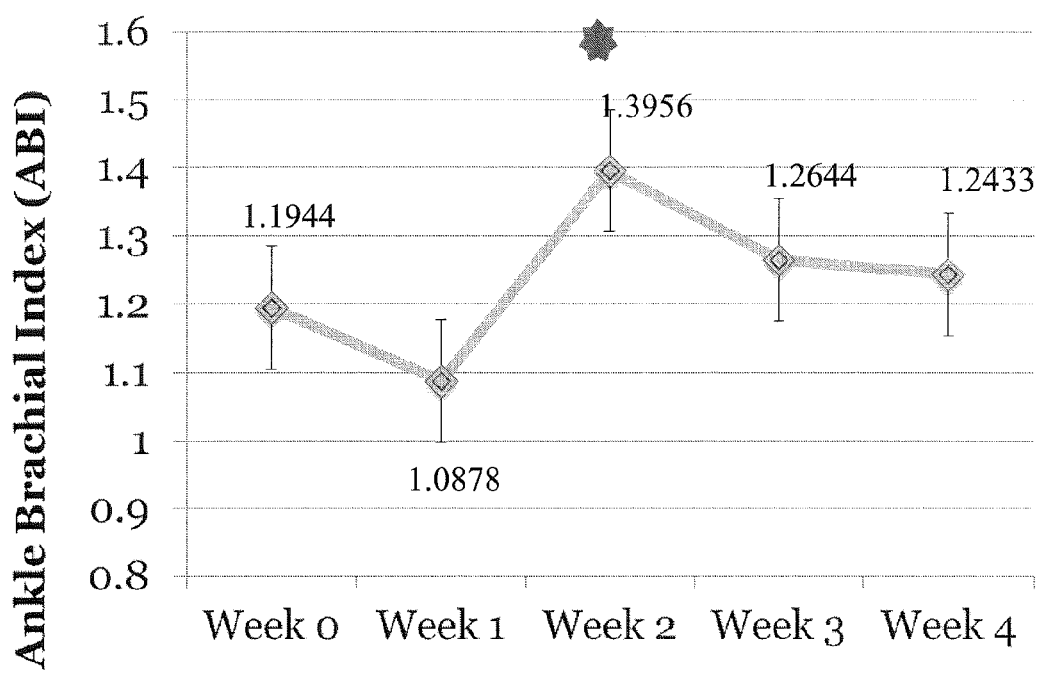

FIG. 7: Change in ankle brachial indices.

Further the invention is explained in more detail by the following examples. A clinical trial was conducted comprising nine diabetic patients with lower extremity edema. The patients received mild compression stockings according to the invention made of Dri Release Yarn® for four consecutive weeks. The patients exhibiting lower extremity edema of the leg, foot and ankle and an Ankle Brachial Index (ABI) over 0.6, however no current infected foot ulcer or untreated osteomyelitis, were recruited from the Food and Ankle Clinic of the Rosalind Franklin University Health System. All patients signed a written consent form following full explanation of the study. Lower extremity edema, vascular status and patient comfort were assessed on a weekly basis.

At the initial visit (week 0) all subjects were subjected a full medical history and completed a standardised physical exam, which included a neurological assessment and a vascular assessment.

Neurological Assessment

The Neurological assessment consists of Vibratory Perception Threshold testing (VPT) using the technique described by Young et al. (Diabetes Care. 1994; 17(6):557-560) and the 10 gram Semmes-Weinstein monofilament test using the criteria described by Armstrong et al. (Archives of Internal Medicine. 1998; 158:289). The presence of sensory neuropathy will be identified as vibratory perception threshold greater than 25 volts or inability to accurately perceive a 10 gram Semmes-Weinstein monofilament at 1 or more of 10 test sites on the sole and dorsum of the foot (Wu et al., Vasc Health Risk Manag. 2007; 3(1):65).

Vascular Assessment:

The vascular assessment consists of palpation of the dorsalis pedis and posterior tibial arteries and non-invasive Doppler studies. Ankle Brachial Index (ABI) will be determined for both extremities (Apelqvist et al., Diabetes Care. 1989; 12:373). ABI ratios less than 0.6 will indicate severe disease. These patients are eliminated from the study per exclusion criteria. Baseline foot (by measuring the midfoot area using the navicular tuberosity as a landmark), ankle (measure made at the narrowest part of the ankle above the lateral malleolus) and calf circumferences (made at the widest width of the calf) is also determined (Brodovicz et al., Clin Med Res. 2009; 7(1-2):21). Further, patient's cutaneous edema/fluid level (via MoistureMeter, Delfintech) values is determined.

The MoistureMeter is a hand-held and battery-operated device with a closed measuring chamber to permit transcutaneous moisture measurements in the clinical setting. The MoistureMeter's cylindrical chamber contains thin-film capacitive sensors (HIH 3605-B, Honeywell) which measure relative moisture and temperature. The sensor is directly integrated into a hand-held microprocessor-controlled electronic unit with a digital readout for transcutaneous moisture and temperature values. The chamber is unaffected by ambient airflows as it is closed by the measured surface during the measurement. The short measuring time ensures that blocking of normal evaporation is minimal. There is an increase of relative humidity (RH) in the chamber shortly after placing the device in contact with the skin.

Before skin contact, the relative moisture level in the measurement chamber is equal to the ambient relative humidity. Values of ambient relative humidity (%) and temperature (° C.) are recorded before skin contact. The evaporation rate value ($g/m^2h$) is calculated from the increase in relative humidity in the chamber after placing the device in contact with the measured skin site. The chamber is passively ventilated between measurements.

The average change per patient at each visit will then be used for further analysis by using a repeated measures ANOVA. SPSS software (Chicago) will be used for the statistical analysis. Only one leg for each patient will be utilized for analysis purposes. This will be the leg that is most edemanous at baseline.

The subjects were instructed to wear the tailor-made stockings at all times while awake. All subjects returned to the clinic within one week±1 day from the previous visit for four consecutive weeks.

At each subsequent study visit (weeks 1-4) the patients were subjected to an investigation of the arterial status (via Ankle Brachial Index (ABI)), Patient's foot, ankle and calf circumferences, and Patient's cutaneous edema/fluid level (via MoistureMeter, Delfintech).

A product evaluation form was also completed at each study visit to assess the amount of time the subjects spent in the stockings, the ease of its application and removal, the ease of care for the stockings and the overall comfort in the stockings (FIG. 2).

100% of the patients responded that they would recommend using the compression stockings, that care for the stockings was moderately or very easy and overall comfort in the stocking was moderately or very comfortable. 66.7% of the patients rated ease of removal of the product at an 8 or above out of 10, and 44.4% rated ease of application at an 8 or above out of 10.

Weekly circumferential measurements for the mid-foot, ankle, and calf are depicted in FIGS. 3, 4, and 5, respectively.

Overall, there was a decrease from week 0 to week 4 in mid-foot (29.1 cm±0.698 for week 0, 28.3 cm±0.533 for week 4), ankle (25.9 cm±0.902 for week 0, 24.1 cm±0.648 for week 4), and calf (41.1 cm±1.489 for week 0, 39.9 cm±1.167 for week 4) circumferences. The greatest decreases are seen between week 0 and week 1.

Weekly cutaneous edema measurements are illustrated in FIG. 6. Although mild weekly fluctuations were noted, there was an overall decrease in cutaneous edema in week 0 to week 4 (32.3 TDC±2.574 for week 0, 29.7 TDC±1.942 for week 4).

The Ankle Brachial Indices are similar in week 0 and week 4 (1.19±0.185 for week 0, 1.24±0.156 for week 4) although weekly fluctuations were noted (FIG. 7). The ABI value variation at week 2 seems to be due to machine error.

The data show an average decrease of 1.2 cm in the calf circumference of the subjects over a period of 4 weeks when using the graduated compression stockings. Studies on venous insufficiency have found that a decrease of 0.6 cm in calf circumference to be significant (Ting et al., Vasc. and Endovascular Surg. 2001, 35(6), 43). The data show consistent trends in an overall reduction of lower extremity edema. Thus, the compression garments according to the present invention are ideally suitable for treating edema in patients suffering from diabetes.

The invention claimed is:

1. A graduated compression garment for legs, the garment comprising:
an ankle zone, a calf zone, an Achilles section, a heel section, a toe section having flat toe seams, and a foot sole section;
wherein pressure at the ankle zone is about 10-27 mmHg and the pressure at the calf zone is about 6-16 mmHg; and
wherein at least one of the Achilles section, heel section, toe section and foot sole section is cushioned with cushioning on an internal side of the garment.

2. The graduated compression garment of claim 1, wherein the heel section is configured such that it covers the heel.

3. The graduated compression garment of claim 2, wherein the heel section changes over the Achilles section or the foot sole section.

4. The graduated compression garment of claim 1, wherein the compression garment comprises at least an elastic yarn and a fiber.

5. The graduated compression garment of claim 4, wherein the elastic yarn is a synthetic yarn or a natural elastic yarn and the fiber is a synthetic or natural fiber, and wherein the synthetic yarn is a spandex yarn and the natural elastic yarn is rubber, and wherein the synthetic or natural fiber is polyamide, polyester, cellulose-based fiber, cotton, or wool.

6. The graduated compression garment of claim 1, wherein the pressure at the ankle zone is about 15-25 mmHg and the pressure at the calf zone is about 9-13 mmHg.

7. The graduated compression garment of claim 1, wherein the cushioning comprises terry loop padding.

8. The graduated compression garment of claim 1, wherein the toe section comprises a base, and the toe section is cushioned and extends beyond the base.

9. The graduated compression garment of claim 1, wherein the foot sole section is cushioned and configured such that it extends beyond the foot sole section to sides of the foot section.

10. The graduated compression garment of claim 1, wherein the Achilles section is cushioned with cushioning that is at least 3 cm in width.

11. The graduated compression garment of claim 1, wherein the compression garment further comprises a chitosan-containing fiber, wherein a surface of the chitosan-containing fiber is at least partially coated with chitosan.

12. A method for treating or preventing edema comprising applying the graduated compression garment of claim 1 to a patient.

13. The method of claim 12, wherein the edema are lower extremity edema.

14. The method of claim 12, wherein the patient suffers from diabetes type I or type II.

15. The method of claim 12, wherein the patient has peripheral arterial occlusive diseases (PAOD) or polyneuropathy and the garment has no negative effect on the PAOD or the polyneuropathy.

16. A graduated compression garment for legs, the garment comprising:
an ankle zone, a calf zone, an Achilles section, a heel section, a toe section having flat toe seams, and a foot sole section;
wherein pressure at the ankle zone is about 10-27 mmHg and the pressure at the calf zone is about 6-16 mmHg; and
wherein at least one of the Achilles section, heel section, toe section and foot sole section is cushioned with cushioning on an internal side of the garment, and
wherein the compression garment comprises an elastic fiber at least partially covered with a chitosan-containing component, the chitosan-containing component in direct contact with skin when the graduated compression garment is applied.

17. A graduated compression garment for legs, the garment comprising:
an ankle zone, a calf zone, an Achilles section, a heel section, a toe section having flat toe seams, and a foot sole section;
wherein pressure at the ankle zone is about 10-27 mmHg and the pressure at the calf zone is about 6-16 mmHg; and
wherein at least one of the Achilles section, heel section, toe section and foot sole section is cushioned with cushioning on an internal side of the garment, and
wherein the compression garment, when applied for treating or preventing edema to a patient suffering from diabetes and peripheral arterial occlusive diseases (PAOD) or polyneuropathy, causes no negative effect on the PAOD or the polyneuropathy.

* * * * *